United States Patent [19]
Fischer et al.

[11] 3,935,190
[45] Jan. 27, 1976

[54] SULFITES OF ALIPHATIC GLYCOLIC AMIDES

[75] Inventors: Adolf Fischer, Mutterstadt; Hanspeter Hansen, Ludwigshafen; Wolfgang Rohr, Mannheim, all of Germany

[73] Assignee: BASF Aktiengesellschaft, Ludwigshafen, Germany

[22] Filed: June 20, 1974

[21] Appl. No.: 481,216

[30] Foreign Application Priority Data
June 30, 1973 Germany............................ 2333477

[52] U.S. Cl..... 260/239 B; 260/239 A; 260/293.85; 260/326.5 S; 71/88; 71/94; 71/95
[51] Int. Cl.².............. C07D 295/16; C07D 223/04
[58] Field of Search ........ 260/456 R, 239 A, 239 B, 260/293.85, 326.5 S

[56] References Cited
UNITED STATES PATENTS

| | | | |
|---|---|---|---|
| 3,775,458 | 11/1973 | Corey............................ | 260/456 R |
| 3,798,254 | 3/1974 | Phillips.......................... | 260/293.85 |

*Primary Examiner*—Richard J. Gallagher
*Assistant Examiner*—Mark L. Berch
*Attorney, Agent, or Firm*—Johnston, Keil, Thompson and Shurtleff

[57] ABSTRACT

New and valuable sulfites of aliphatic glycolic amides having a good herbicidal action, herbicides containing these compounds, and a process for controlling the growth of unwanted plants with these compounds.

5 Claims, No Drawings

SULFITES OF ALIPHATIC GLYCOLIC AMIDES

The present invention relates to new and valuable sulfites of aliphatic glycolic amides and herbicides containing them, and their use for controlling unwanted plant growth.

It is known (German Pat. No. 1,014,380) to use N-isopropyl-α-chloroacetanilide for controlling unwanted plants in crops such as Indian corn, soybeans and vegetables. However, its action is not satisfactory.

We have now found that sulfites of aliphatic glycolic amides of the formula

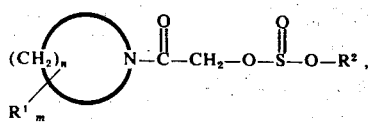

where $R^1$ denotes alkyl, e.g., methyl and ethyl, m denotes one of the integers 0, 1, 2 and 3, $R^2$ denotes an aliphatic radical of from 1 to 6 carbon atoms, e.g., methyl, ethyl, propyl, isopropyl, butyl, sec-butyl and tert-butyl, which may be mono- or polysubstituted by halogen or alkoxy, $R^2$ further denotes cyclopropyl, cyclohexyl, alkenyl or alkynyl, e.g., allyl, methallyl, propargyl and butyn-1-yl-3, and n denotes one of the integers 3, 4, 5 and 6, have a good herbicidal action. They have better crop plant compatibility and a better herbicidal action than N-isopropyl-α-chloroacetanilide.

The active ingredients may be prepared by reacting, at 10° to 15°C, an alkyl chlorosulfinate with a glycolic amide in an inert solvent in the presence of a compound which binds hydrogen chloride.

EXAMPLE 1

Preparation of 1H-azepineacetamido-α-ethyl sulfite 15.7 parts (by weight) of 1H-azepine glycolic amide is dissolved together with 8.0 parts of pyridine in 50 parts of dry benzene. At 10° to 15°C, 12.9 parts of ethyl chlorosulfinate dissolved in 50 parts of benzene is dripped in.

After 30 minutes the precipitated pyridinium hydrochloride is suction filtered and the organic phase is washed with water. After drying, the benzene is distilled off. There is obtained 20.4 parts of the desired product having the following structure:

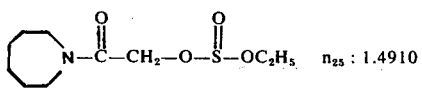  $n_{25}$ : 1.4910

The following compounds may be prepared in the same manner:

| | |
|---|---|
| 1H-azepine acetamido-α-methyl sulfite | $n_{25}$: 1.4955 |
| 1H-azepine acetamido-α-isopropyl sulfite | $n_{25}$: 1.4695 |
| 1H-azepine acetamido-α-butyl sulfite | $n_{25}$: 1.4875 |
| pyrrolidine acetamido-α-propyl sulfite | $n_{25}$: 1.4828 |
| pyrrolidine acetamido-α-isopropyl sulfite | m.p.: 58° to 59°C |
| 2-methyl-1H-azepine acetamido-α-ethyl sulfite | $n_{25}$: 1.4882 |
| 2-methyl-1H-azepine acetamido-α-isopropyl sulfite | $n_{25}$: 1.4740 |
| 2,3-dimethyl-1H-azepine acetamido-α-methyl sulfite | $n_{25}$: 1.4952 |
| 2,3-dimethyl-1H-azepine acetamido-α-ethyl sulfite | $n_{25}$: 1.4860 |
| 2,3-dimethyl-1H-azepine acetamido-α-propyl sulfite | $n_{25}$: 1.4849 |
| 2,3-dimethyl-1H-azepine acetamido-α-isopropyl sulfite | $n_{25}$: 1.4749 |
| 3,5,5-trimethyl-(3,3,5-trimethyl)-1H-azepine acetamido-α-ethyl sulfite (1 : 1 isomer mixture of the 3,3,5- and 3,5,5-trimethyl derivative) | $n_{25}$: 1.4850 |
| 3-methyl-(2-methyl)-1H-azepine acetamido-α-isopropyl sulfite (isomer mixture consisting to the extent of 55% of the 3-methyl- and 45% of the 2-methyl derivative) | $n_{25}$: 1.4735 |
| 2-methyl-(3-methyl)-1H-azepine acetamido-α-isopropyl sulfite (isomer mixture consisting to the extent of 75% of the 2-methyl- and 25% of the 3-methyl derivative) | $n_{25}$: 1.4698 |
| 2,3-dimethyl-1H-azepine acetamido-α-allyl sulfite | $n_{25}$: 1.4970 |
| 1H-azepine acetamido-α-allyl sulfite | $n_{25}$: 1.5026 |
| 2,3-dimethyl-1H-azepine acetamido-α-(butyn-1-yl-3)-sulfite | $n_{25}$: 1.4929 |
| 3-methyl-1H-azepine acetamido-α-(butyn-1-yl-3-)-sulfite | $n_{25}$: 1.4965 |
| piperidine acetamido-α-ethyl sulfite | |
| piperidine acetamido-α-isopropyl sulfite | |
| 2-methylpiperidine acetamido-α-methyl sulfite | |
| 2-methylpiperidine acetamido-α-allyl sulfite | |
| 2-methylpiperidine acetamido-α-isopropyl sulfite | |
| 3-methylpiperidine acetamido-α-isopropyl sulfite | |
| 3-methylpiperidine acetamido-α-(β-chloroethyl sulfite) | |
| 4-methylpiperidine acetamido-α-ethyl sulfite | |
| 4-methylpiperidine acetamido-α-allyl sulfite | |
| 4-methylpiperidine acetamido-α-(β-chloroethyl sulfite) | |
| 3,3-dimethylpiperidine acetamido-α-methyl sulfite | |
| 3,3-dimethylpiperidine acetamido-α-isopropyl sulfite | |
| 3,5,5-trimethyl-(3,5,5-trimethyl)-1H-azepine acetamido-α-(β-chloroethyl sulfite) (1 : 1 isomer mixture of the 3,5,5- and the 3,3,5-trimethyl derivative). | |

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as
Cynodon spp.
Digitaria spp.
Echinochloa spp.
Setaria spp.
Panicum spp.
Alopecurus spp.
Lolium spp.
Sorghum spp.
Agropyron spp.
Phalaris spp.
Apera spp.
etc.;
Dactylis spp.
Avena spp.
Bromus spp.
Uniola spp.
Poa spp.
Leptochloa spp.
Brachiaria spp.
Eleusine spp.
Cenchrus spp.
Eragrostis spp.
Phragmites communis Cyperaceae, such as
Carex spp.
Cyperus spp.
etc.;
Eleocharis spp.
Scirpus spp.

dicotyledonous weeds, such as

Malvaceae, e.g.,
Abutilon theoprasti
Sida spp.
etc.;
Hibiscus spp.
Malva spp.

Compositae, such as
Ambrosia spp.
Lactuca spp.
Senecio spp.
Sonchus spp.
Xanthium spp.
Iva spp.
Galinsoga spp.
Taraxacum spp.
Chrysanthemum spp.
Cirsium spp.
Centaurea spp.
Tussilago spp.
Lapsana communis
Tagetes spp.
Erigeron spp.
Anthemis spp.
Matricaria spp.
Artemisia spp.
Bidens spp.
etc.;

Convolvulaceae, such as
Convolvulus spp.
Ipomoea spp.
etc.;
Cuscuta spp.
Jaquemontia tamnifolia Cruciferae, such as
Barbarea vulgaris
Brassica spp.
Capsella spp.
Sisymbrium spp.
Thlaspi spp.
Sinapis arvensis
etc.;
Arabidopsis thaliana
Descurainia spp.
Draba spp.
Coronopus didymus
Lepidium spp.
Raphanus spp.

Geraniaceae, such as
Erodium spp.
etc.;
Geranium spp.

Portulacaceae, such as
Portulaca spp.
etc.;

Primulaceae, such as
Anagallis arvensis
etc.;
Lysimachia spp.

Rubiaceae, such as
Richardia spp.
Galium spp.
Diodia spp.
etc.;

Scrophulariaceae, such as
Linaria spp.
Veronica spp.
Digitalis spp.
etc.;

Solanaceae, such as
Physalis spp.
Solanum spp.
etc.;
Nicandra spp.
Datura spp.

Urticaceae, such as
Urtica spp.

Violaceae, such as
Viola spp.
etc.;

Zygophyllaceae, such as
Tribulus terrestris
etc.;

Euphorbiaceae, such as
Mercurialis annua
Euphorbia spp.

Umbelliferae, such as
Daucus carota
Aethusa cynapium
Ammi majus
etc.;

Commelinaeae, such as
Commelina spp.
etc.;

Labiatae, such as
Lamium spp.
etc.;
Galeopsis spp.

Leguminosae, such as
Medicago spp.
Trifolium spp.
Vicia spp.
etc.;
Sesbania exaltata
Cassia spp.
Lathyrus spp.

Plantaginaceae, such as
Plantago spp.
etc.;

Polygonaceae, such as
Polygonum spp.
Rumex spp.
Fagopyrum spp.
etc.;

Aizoaceae, such as
Mollugo verticillata
etc.;

Amaranthaceae, such as
Amaranthus spp.
etc.;

Boraginaceae, such as
Amsinckia spp.
Myostis spp.
etc.;
Anchusa spp.
Lithospermum spp.

Caryophyllaceae, such as
Stellaria spp.
Spergula spp.
Saponaria spp.
Scleranthus annuus
Silene spp.
Cerastium spp.
Agrostemma githago
etc.;

Chenopodiaceae, such as
Chenopodium spp.
Kochia spp.
Salsola Kali
Atriplex spp.
Monolepsis nuttalliana
etc.;

Lythraceae, such as
Cuphea spp.
etc.;

Oxalidaceae, such as
Oxalis spp.

Ranunculaceae, such as
Ranunculus spp.
Delphinium spp.
Adonis spp.
etc.;

Papaveraceae, such as
Papaver spp.
etc.;
Fumaria officinalis

Onagraceae, such as
Jussiaea spp.
etc.;

Rosaceae, such as
Alchemillia spp.
etc.;
Potentilla spp.

Potamogetonaceae, such as
Potamogeton spp.
etc.;

Najadaceae, such as
Najas spp.
etc.;

Marsileaceae, such as
Marsilea quadrifolia
etc.

The new agents may be employed in cereal crops such as

Avena spp.
Triticum spp.
Hordeum spp.
Secale spp.
Sorghum
Zea mays
Panicum miliaceum
Oryza spp.

and in dicotyledon crops such as

Cruciferae, e.g.,
Brassica spp.
Sinapis spp.
Raphanus spp.
Lepicium spp.

Compositae, e.g.,
Lactuca spp.
Helianthus spp.
Carthamus spp.
Scorzonera spp.

Malvaceae, e.g.,
Gossypium hirsutum

Leguminosae, e.g.,
Medicago spp.
Trifolium spp.
Pisum spp.
Phaseolus spp.
Arachis spp.
Glycine max.

Chenopodiaceae, e.g.,
Beta vulgaris
Spinacia spp.

Solanaceae, e.g.,
Solanum spp.
Nicotiania spp.
Capsicum annuum

Linaceae, e.g.,
Linum spp.

Umbelliferae, e.g.,
Petroselinum spp.
Daucus carota
Apium graveolens

| | |
|---|---|
| Rosaceae, e.g., | |
| Fragaria | |
| Cucurbitaceae, e.g., | |
| Cucumis spp. | Cucurbita spp. |
| Liliaceae, e.g., | |
| Allium spp. | |
| Vitaceae, e.g., | |
| Vitis vinifera | |
| Bromeliaceae, e.g., | |
| Ananas sativus | |

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or mineral origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients (if desired, immediately before use (tankmix)) oils of various types, herbicides, fungicides, nematocides, insecticides, bactericides, trace elements, fertilizers, antifoams (e.g., silicones), growth regulators, antidotes and other herbicidally effective compounds such as substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides.
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The amount used of the agents according to the invention may vary and depends in essence on the type of effect to be achieved; it is generally from 0.1 to 15 (and more) kg per hectare, preferably from 0.2 to 6 kg per hectare, of active ingredient. The agents according to the invention may be used before or after planting, before sowing, pre- and postemergence, or during emergence of the crop or unwanted plants.

EXAMPLE 2

In the greenhouse, loamy sandy soil was filled into pots and sown with various seeds. The soil prepared in this manner was then immediately treated with 3 kg per hectare of each of active ingredients I, II, IV, V and VI, and, for comparison, with 3 kg per hectare of III, each compound being emulsified or dispersed in 500 liters of water per hectare.

Active ingredients:

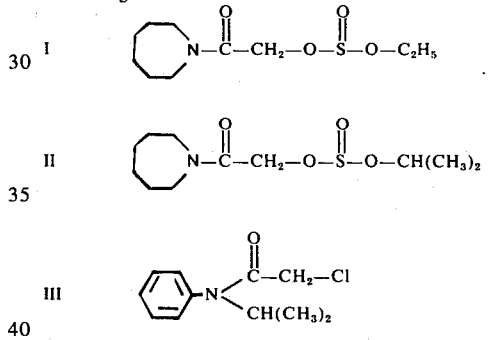

IV  3-methyl-(4-methyl)-1-H-azepine acetamido-α-isopropyl sulfite (isomer mixture)
V   2-methyl-1-H-azepine acetamido-α-isopropyl sulfite
VI  1-H-azepine acetamido-α-n-propyl sulfite After 3 to 4 weeks it was ascertained that active ingredients I, II, IV, V and VI have better crop plant compatibility and a better herbicidal action than compound III.

The results are given below:

| Active ingredient kg/ha | I 3 | II 3 | III 3 | IV 3 | V 3 | VI 3 |
|---|---|---|---|---|---|---|
| Crop plants: | | | | | | |
| Brassica napus | 0 | 0 | 0 | 0 | 0 | 0 |
| Glycine hispida | 0 | 0 | 0 | 0 | 0 | 0 |
| Zea mays | 0 | 0 | 0 | 0 | 0 | 0 |
| Gossypium hirsutum | 0 | 0 | 0 | 0 | 0 | 0 |
| Beta vulgaris | 0 | 0 | 0 | 0 | 0 | 0 |
| Unwanted plants: | | | | | | |
| Lolium multiflorum | 100 | 100 | 90 | 100 | 100 | 100 |
| Lolium perenne | 100 | 100 | 80 | 100 | 100 | 100 |
| Echinochloa crus-galli | 80 | 100 | 80 | 100 | 95 | 100 |
| Digitaria sanguinalis | 80 | 100 | 70 | 100 | 95 | 100 |
| Setaria viridis | 80 | 100 | 70 | 100 | 95 | 100 |
| Poa trivialis | 100 | 100 | 80 | 100 | 100 | 100 |
| Poa annua | 100 | 100 | 75 | 100 | 100 | 100 |

0 = no damage
100 = complete destruction

EXAMPLE 3

In the greenhouse, various plants were treated with 3 kg per hectare of each of I, II, IV, V and VI and, for comparison, 3 kg per hectare of III, each compound being emulsified or dispersed in 500 liters of water per hectare. After 3 to 4 weeks it was ascertained that active ingredients I, II, IV, V and VI had a better herbicidal action than III, combined with the same good crop plant compatibility.

The results are given below:

| Active ingredient kg/ha | I 3 | II 3 | III 3 | IV 3 | V 3 | VI 3 |
|---|---|---|---|---|---|---|
| Crop plants: | | | | | | |
| Brassica napus | 0 | 0 | 0 | 0 | 0 | 0 |
| Glycine hispida | 0 | 0 | 0 | 0 | 0 | 0 |
| Zea mays | 0 | 0 | 0 | 0 | 0 | 0 |
| Gossypium hirsutum | 0 | 0 | 0 | 0 | 0 | 0 |
| Beta vulgaris | 0 | 0 | 0 | 0 | 0 | 0 |
| Unwanted plants: | | | | | | |
| Lolium multiflorum | 100 | 100 | 40 | 40 | 100 | 95 |
| Lolium perenne | 100 | 100 | 40 | 100 | 100 | 95 |
| Echinochloa crus-galli | 100 | 100 | 30 | 95 | 100 | 95 |
| Digitaria sanguinalis | 100 | 100 | 35 | 95 | 100 | 95 |
| Setaria viridis | 100 | 100 | 40 | 95 | 100 | 100 |
| Poa trivialis | 100 | 100 | 45 | 100 | 100 | 100 |
| Poa annua | 100 | 100 | 45 | 100 | 100 | 100 |

0 = no damage
100 = complete destruction

The action of the following compounds corresponds to that of I, II, IV, V and VI in the foregoing examples:

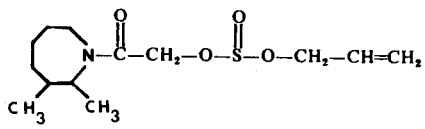

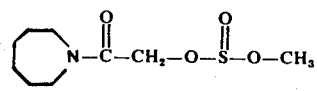

EXAMPLE 4

90 parts by weight of compound I is mixed with 10 parts by weight of N-methyl-α-pyrrolidone. A mixture is obtained which is suitable for application in the form of very fine drops.

EXAMPLE 5

20 parts by weight of compound II is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound V is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound I is dissolved in a mixture consisting of 25 parts by weight of cyclohexanol, 65 parts by weight of a mineral oil fraction having a boiling point between 210° and 280°C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound II is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 9

3 parts by weight of compound V is intimately mixed with 97 parts by weight of particulate kaolin. A dust is obtained containing 3% by weight of the active ingredient.

EXAMPLE 10

30 parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. A sulfite of an aliphatic glycolic amide of the formula

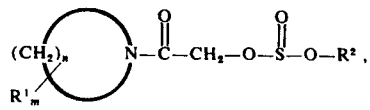

where R$^1$ is methyl or ethyl, m denotes one of the integers 0, 1, 2 and 3, R$^2$ is selected from the group consisting of alkyl of 1 to 6 carbons, alkyl of 1 to 6 carbon atoms none-substituted by halogen; cyclopropyl; cyclohexyl; allyl; methallyl; propargyl; and butyn-1-yl-3, and n denotes one of the integers 3, 4, 5 and 6.

2. 1H-azepine acetamido-α-ethyl sulfite.
3. 1H-azepine acetamido-α-isopropyl sulfite.
4. 2-methyl-1H-azepine acetamido-α-isopropyl sulfite.
5. A sulfite as set forth in claim 1 wherein said halogen is chlorine.

* * * * *